United States Patent
Chan

(10) Patent No.: US 9,968,645 B2
(45) Date of Patent: May 15, 2018

(54) METHOD FOR ENHANCED PRODUCTION OF MORINDA METABOLITES

(71) Applicant: Sham Yuen Chan, Malvern, PA (US)

(72) Inventor: Sham Yuen Chan, Malvern, PA (US)

( * ) Notice: Subject to any disclaimer, the term of this patent is extended or adjusted under 35 U.S.C. 154(b) by 150 days.

(21) Appl. No.: 14/983,805

(22) Filed: Dec. 30, 2015

(65) Prior Publication Data

US 2016/0220625 A1 Aug. 4, 2016

Related U.S. Application Data

(60) Provisional application No. 62/098,781, filed on Dec. 31, 2014.

(51) Int. Cl.
| | | |
|---|---|---|
| *A61K 36/00* | (2006.01) | |
| *A61K 36/746* | (2006.01) | |
| *A61K 31/7048* | (2006.01) | |
| *A61K 31/122* | (2006.01) | |
| *C12N 15/82* | (2006.01) | |
| *A61K 31/366* | (2006.01) | |

(52) U.S. Cl.
CPC .......... *A61K 36/746* (2013.01); *A61K 31/122* (2013.01); *A61K 31/366* (2013.01); *A61K 31/7048* (2013.01); *C12N 15/8205* (2013.01); *C12N 15/8243* (2013.01)

(58) Field of Classification Search
CPC ..................................................... A61K 36/00
See application file for complete search history.

(56) References Cited

U.S. PATENT DOCUMENTS

| | | | |
|---|---|---|---|
| 4,588,693 | A | 5/1986 | Strobel |
| 7,202,397 | B2 | 4/2007 | Conceicao et al. |
| 7,223,424 | B2 | 5/2007 | Chou |
| 2011/0217394 | A1 | 9/2011 | West et al. |

FOREIGN PATENT DOCUMENTS

KR 2005092313 A * 9/2005

OTHER PUBLICATIONS

Koes et al., Trends in Plant Sciences, 10(5):236-242 (2005).
Dixon et al., Plant Cell 7:1085-1097 (1995).
Atschul et al., 1997, Nucleic Acid Res. 25:3389.
Atschul et al., 2005, FEBS J. 272:5101.
Bao et al., 2011, "Anthraquinone compounds from Morinda officinalis, inhibit osteoclastic bone resorption in vitro". Chemico-Biological Interactions 194(2-3): 97-105.
Choi et al. (2005) "Antinociceptive anti-inflammatory effect of Monotropein isolated from the root of Morinda officinalis" Biol Pharm Bull 28 (10): 1915-8.
Ke et al. (2012) "Herbal Medicine in the Treatment of Ulcerative Colitis" Saudi J Gastroenterol 18:3-10.
Li et al. (2009) "Inhibitory Effects of Morinda officinalis Extract on Bone Loss in Ovariectomized Rats" Molecules 14:2049-2061.
Low et al. (2013) "Animal models of ulcerative colitis and their application in drug research" Drug Design, Development and Therapy 7:1341-1357.
Palladino et al. (2003) "Anti-TNF-a Therapies: The Next Generation", Nature Reviews 2:736-746.
Pistelli et al. (2010) "Hairy Root Cultures for Secondary Metabolites Production" Bio-Farms for Nutraceuticals: Functional Food and Safety Control by Biosensors. Chapter 13: 168-184.
Ruoyi, Z. (2010) "Protective effects of polysaccharides extracted from Morinda Officinalis on fetal rat hippocampal neurons" Hong Kong, The University of Hong Kong.
Samaan et al. (2014) "An Update on Anti-TNF Agents in Ulcerative Colitis" Gastroenterology Clinics of North America 43(3):479-494.
Shin et al. (2013) "Monotropein isolated from the roots of Morinda officinalis ameliorates proinflammatory mediators in RAW 264.7 macrophages and dextran sulfate sodium (DSS)-induced colitis via NF-B inactivation" Food and Chemical Toxicology 53:263-271.
Soon et al. (2002) "Evaluation of the hypoglycemic and anti-oxidant activities of Morinda officinalis in streptozotocin-induced diabetic rats" Singapore Med J 43(2):077-085.
Wu et al. (2009) "Antiosteoporotic Activity of Anthraquinones from Morinda officinalis on Osteoblasts and Osteoclasts" Molecules 14:573-583.
Yoshikawa et al. (1996) "ChemInform Abstract: Chemical Constituents of Chinese Natural Medicine, Morindae Radix, the Dried Roots of Morinda officinalis How: Structures of Morindolide and Morothcinaloside" ChemInform 27(12).
Zhou et al. (2011) "Production and metabolic engineering of bioactive substances in plant hairy root culture" Appl Microbiol Biotechnol 90:1229-1239.
Pharmacopeia of the People's Republic of China (2010 edition), Morinda officinalis How (MO) / Bajitian, p. 75.

* cited by examiner

*Primary Examiner* — Qiuwen Mi
(74) *Attorney, Agent, or Firm* — Buchanan Ingersoll & Rooney PC

(57) ABSTRACT

This invention concerns a genetic transformation method to induce hairy root culture of *Morinda* species, such as *Morinda officinalis* How, to increase production of therapeutically useful metabolites, related extracts of the roots, and methods to treat ulcerative colitis using extracts of *Morinda* species, such as *Morinda officinalis* How.

12 Claims, 15 Drawing Sheets

SEQ ID NO: 1

ATGGTGAGCGTCGAGGAATTCTGCCGTGCCCAGAAATCGAAAGGCCCTGCCTCGGTCCTCGCCATCGGAACGGCG
GTCCCCAAGAACGTCATCGAGCAGAGCACATACCCGGATTATTTGTTTCGGATCACCAACAGCGAGCACATGACCG
AGCTGAAAGAGAAGTTCAAGCGCATGTGTATGTATAGTTCAAAGCATACCTACATTGATGCTCTTTCATTTATATGT
AATTTTTTTGCTGCGCCCTCATCATTTATCATCACGTAAGAATTTGCCGGATTCACTTCATCTAGCGTATCCATGCTT
TAGATAAGAAATTAAGGAAAGACGGTGAAAGCAAATCAACAGTAGTTTCGATGGGAGTTCCCGATGCCAGGATC
GGTTTTCTTCCGGTAATAACTTGTGGGGTCATTGAAAAGATTGCGCCCTTCATCGTCGCGTACCATTAGCTCGATCG
GTCCGTAGAGAAGGACTATAAAAAAGGCGTCGCAGGGGCTCATTGACATGGGGTCTGTGTTTGGTTTGTGTATGT
TTCAGGTGAGGGGTCGTCGATCAAGAGGAGATACGTGCACATGACGGAGGATATATTGAAAGAGCACCCGAGCA
TGAGTTCATTCACGGAACCCTCCTTGGATGCCCGGCACGACATCCTGGTGTCGGAAGTGCCGAAGCTGGCGAAGG
AGGCGGCGGCGAACGCCCTGAAGGAATGGGGGCAGCCCAAGTCGAAGATCACCCACCTGGTGTTCTGCACCACC
AGCGGTGTCGACATGCCGGCTGCGACTACCAGCTCACCAAGCTCCTGGGCCTCCGCCCCACCGTCAAGCGGTAC
ATGATGTACCAGGTGGGCTGCTACGGCGCTGGCCTGGTCCTCCGCATCGCCAGGGATCTTGCTGAGAACAACAAG
GGGGCTCGCGTCCTCGTCGTGTGCGCCGAGATCACCGTCTGCACCTTCCGCGGCCCCACCGAGACCTACCTGGACA
ACCTCGTGGGCCAGGCTCTGTTCGGCGATGGCGCCTCCTCGGTCATCGTGGGCTCGGACCCCGTCCCGGGGGTCG
AGAGGCCCCTGTACGAGATCGTCTCCACCTCCCAGACTCTCCTCCCAAACAGCGAGGGGGCCATTGCTGGGCACG
TCCGGGAGATCGGGCTCACCATCCACCTCCTCAAGGACGTGCCGGGCCTCATCTCCAAGAACGTCGAGAAGAACA
TGACTGAGGCGTTCCACCCACTGGGCATCACCGACTGGAACTCGCTCTTCTTCATCGTGCACCCCGGCGGGCCCGC
GATTCTCGACGAGGTCGAGGCCAAGTTGAAGCTCAAGCCCGAGAAGATGGAGGCTTCCAGGTATGTGCTCGGCG
AGTATGGCAACATGTCTAGCGCATGCGTCTTCTTCATAATGGACGAGATGAGGAAGAAATCGATCAAGAAAGGGC
TCAAGACCACTGGAGAGGGGCTCGAATGGGGCGTGCTCTTCGGATTTGGTCCCGGCCTCACCGTCGAGACCGTCG
TCCTCCACGCCCTGTCTGCTTAA

FIG. 3A

SEQ ID NO: 2

MVSVEEFCRAQKSKGPASVLAIGTAVPKNVIEQSTYPDYLFRITNSEHMTELKEKFKRMCEGSSIKRRYVHMTEDILKEH
PSMSSFTEPSLDARHDILVSEVPKLAKEAAANALKEWGQPKSKITHLVFCTTSGVDMPGCDYQLTKLLGLRPTVKRYM
MYQVGCYGAGLVLRIAKDLAENNKGARVLVVCAEITVCTFRGPTETYLDNLVGQALFGDGASSVIVGSDPVPGVERPLY
EIVSTSQTLLPNSEGAIAGHVREIGLTIHLLKDVPGLISKNVEKNMTEAFHPLGITDWNSLFFIVHPGGPAILDEVEAKLKLK
PEKMEASRYVLGEYGNMSSACVFFIMDEMRKKSIKKGLKTTGEGLEWGVLFGFGPGLTVETVVLHALSA

FIG. 3B

METHOD FOR ENHANCED PRODUCTION OF MORINDA METABOLITES

BACKGROUND

*Morinda officinalis* How (MO), a member of the Rubiaceae family, is a small vine that grows widely in tropical and subtropical regions. The roots of this plant (named Bajitian) have been recorded in the pharmacopeia of the People's Republic of China (2010 edition) to help strengthen the bones and kidneys and to enhance the immune system function. In contrast to Western countries, in eastern Asia, particularly in China, herbal therapies have been common throughout centuries. The roots of *Morinda officinalis* continue to be traditionally used to treat rheumatoid arthritis, diabetes and hypertension in North East Asia (Choi, J. et al., 2005). This plant has also been used to treat impotence, menstrual disorders, and other inflammatory diseases such as dermatitis. Compositions including components derived from many plants, including Radix Morindae Officinalis, have been disclosed as agents for the treatment of cancer and other disorders of the prostate and (U.S. Pat. No. 7,223,424 to Wen Hsien Chou).

A number of constituents have been isolated from *Morinda officinalis*. These include iridoid glycosides, anthraquinones, and oligosaccharides. The pharmacological effects of some of these constituents have been identified. Iridoids are a class of secondary metabolites found in a wide variety of plants and in some animals (U.S. Patent Application No. 20110217394). Iridoids were found to possess a wide range of bioactivities, including anti-inflammatory (Shin et al., 2013) and antinoiceptive activities. Several anthraquinones have also been shown to have anti-osteoporotic activity.

The flavonoid biosynthetic pathway is well established and has been widely studied in a number of different plant species (see, for example, Koes et al., Trends in Plant Sciences, 10(5):236-242(2005)). Chalcone synthase (E.C, 2.3.1.74) is the first enzyme in the flavonoid-specific branch of the phenylpropanoid biosynthetic pathway (Dixon et al., Plant Cell7:1085-1097 (1995)). As such it is a key enzyme in secondary metabolism (U.S. Pat. No. 7,202,397).

MO has a 5-7 year growth cycle. Years 1-5 is the growth phase and years 6-7 is the harvest phase. Due to the high medicinal value of its secondary metabolites, MO has been exhaustively excavated in the wild. These secondary metabolites are not essential for plant growth and hence are produced in small amounts (Zhou et. al., 2011). Thus, high numbers of plants are needed for therapeutic amounts, which intensify the foraging and subsequent depletion of wild plants. There is an urgent need to create alternative sources of these metabolites to support patient needs.

Inflammatory bowel disease (IBD) is a type of autoimmune disease in which the body's own immune system attacks elements of the digestive system. One IBD subtype, ulcerative colitis (UC), is an idiopathic chronic relapsing-remitting inflammatory disorder that affects the colon, characterized by diarrhea and rectal bleeding. Current drug treatment for UC patients includes 5 aminosalicyclic acid (5-ASA), corticosteroids, thiopurines, and anti-TNF antibodies. These agents aim to control the extent of inflammation by immunosuppression. However, long-term efficacy is achieved only in approximately one-third of the patients with moderate to severe disease and is frequently accompanied by adverse effects such as risks of infections, lymphoma, and skin cancer.

SUMMARY OF THE INVENTION

One aspect of this invention is based on a surprising discovery that an extract of MO hairy roots is efficacious in treating dextran sulfate-induced colitis in mice. The extract of *Morinda officinalis* How contains iridoids and anthraquinones. Preferably, the extract contains iridoids in an amount ranging from 0.20% to 5% of the dry weight of the extract; and/or anthraquinones in an amount ranging from greater than 0 to less than 1% of the dry weight of the extract. More preferably, the iridoids contain monotropeins in an amount ranging from 0.25% to 2.5% of the dry weight of the extract; and/or deacetylasperulosidic acid in an amount ranging from 0.1% to 2.0% of the dry weight of the extract. It is particularly preferred that the anthraquinones contain rubiadin-1-methyl ether in an amount ranging from 0.001% to 0.15% of the dry weight of the extract.

One aspect of this invention relates to a method of treating ulcerative colitis using hairy roots of MO and extracts thereof.

Another aspect of the invention relates to a method of enhancing the production of secondary metabolites in MO roots via the use of *Agrobacterium rhizogenes* to introduce a nucleotide sequence encoding chalcone synthase (CHS) into the genome of MO (FIG. 1). This gene transduction method has been optimized to generate stable hairy root cultures of MO (FIG. 2) with high productivities for its secondary metabolites. Hairy roots are differentiated cultures of transformed roots derived from the infection of host plant (MO) and *A. rhizogenes*. The genetically transformed roots are capable of unlimited growth in the absence of growth hormones and long-term production of secondary metabolites.

A further aspect of the invention relates to an isolated nucleic acid molecule comprising a nucleotide sequence having at least 90%, 95%, or 100% sequence identity to the cDNA nucleotide sequence of SEQ ID NO:1 and/or encoding an amino acid sequence having at least 90%, 95%, or 100% sequence identity to the amino acid sequence of SEQ ID NO:2. Another aspect of the invention relates to an expression vector comprising a nucleotide sequence encoding a CHS gene.

Also within the scope of this invention is a composition containing the extract of MO hairy roots described above for use in treating UC as well as the use of such composition for the manufacture of a medicament for treating UC.

BRIEF DESCRIPTION OF THE DRAWINGS

The foregoing will be apparent from the following more particular description of example embodiments of the invention, as illustrated in the accompanying drawings.

FIGS. 3A and 3B show the nucleotide sequence of the *E. camaldulensis* CHS cDNA (SEQ ID NO: 1) and the translated amino acid sequence of the *E. camaldulensis* CHS cDNA (SEQ ID NO:2), respectively.

FIG. 6A is a pre-culture of explants. FIG. 6B is the incubation of explants with *Agrobacterium rhizogenes*. FIG. 6C shows decontamination of the explants in 300 mg/l Cefotaxime. FIG. 6D shows the growth of root-like structures (arrows). FIG. 6E depicts an independent culture of a root-like structure. FIG. 6G depicts the rapid growth of hairy roots.

FIG. 9A shows the iridoid profile of a methanolic extract of MO hairy roots. HPLC conditions: Mobile phase: A: 0.4% H3PO4, B: Methanol, Flow rate: 1.000 ml/min, Gradient elution: 0~13 min, A : 95%; 13~14 min, A: 95~91.6%; 14~65 min, A: 91.6~91.3%; 65~70 min, A: 91.3~86%; 70~175 min, A 86~84%; 75~100 min, A 84~80.5%; 100~105 min, A: 80.5~95%. Column temperature: 25.00° C. Detector wave length=233 nm. FIG. 9B shows the anthraquinone profile of a methanolic extract of MO hairy roots. HPLC conditions: Mobile phase A: 0.2% H3PO4, B: Acetonitrile, Flow rate: 1.000 ml/min, Elution gradient: 0~15 min, A: 90~80%; 15~50 min, A: 80~70%; 50~70 min, A: 70~60%; 70~100 min, A: 60~50%; 100~120 min, A: 50~20%; 120~125 min, A: 20%; 125~130 min, A: 20~90%, Column temperature: 30.00° C. Detector wavelength: 277 nm Injection volume=15.00 µL.

DETAILED DESCRIPTION OF INVENTION

Figure 1:
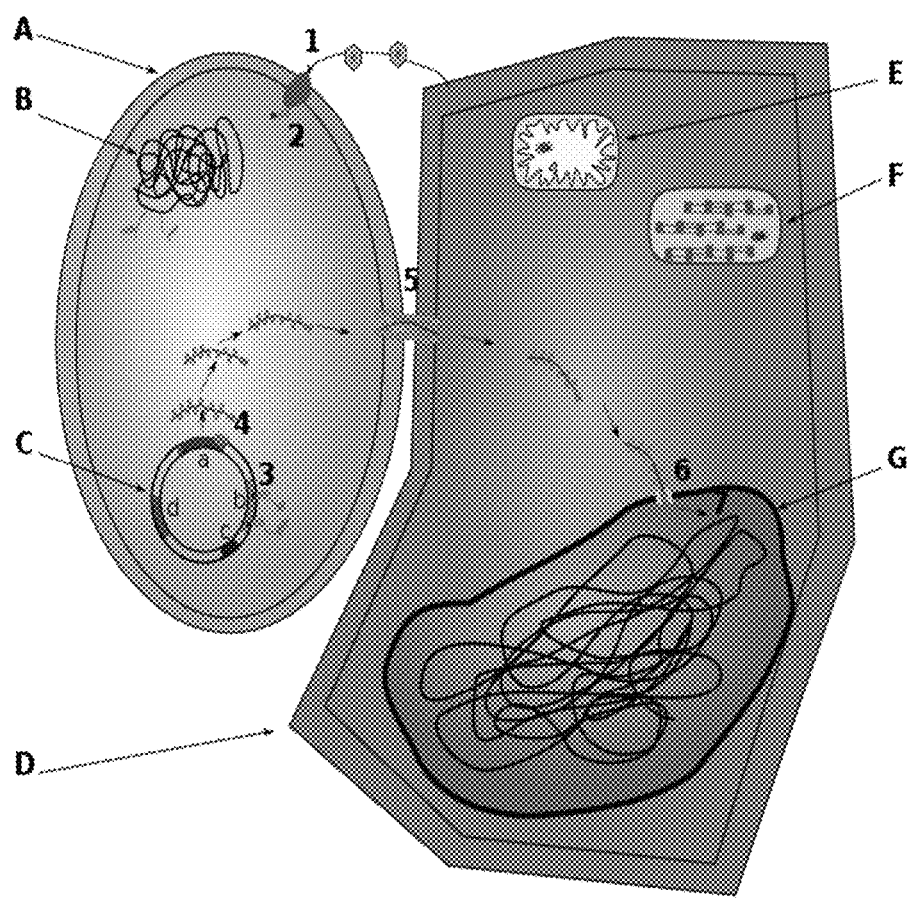
FIG. 1 depicts gene transduction in MO by *Agrobacterium rhizogenes*.
Figure 2:
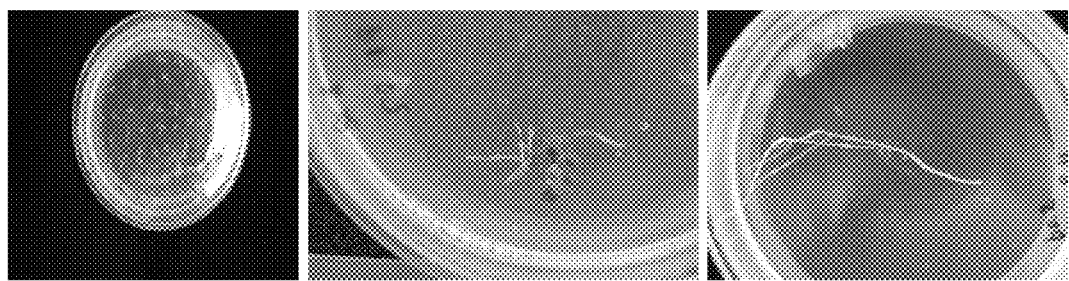
FIG. 2 depicts the induction of hairy roots.

A description of the example embodiments of the invention follows.

Definitions

The present invention may be understood more readily by reference to the following detailed description of preferred embodiments of the invention and the methods included therein. Before the present methods and techniques are disclosed and described, it is to be understood that this invention is not limited to specific analytical or synthetic methods as such may, of course, vary. It is also to be understood that the terminology used herein is for the purpose of describing particular embodiments only and is not intended to be limiting. Unless defined otherwise, all technical and scientific terms used herein have the meaning commonly understood by one of ordinary skill in the art to which this invention belongs.

As used herein, the singular forms "a," "an," and the include plural reference unless the context clearly dictates otherwise. Thus, for example, reference to "a bacterium" is reference to one or more bacteria and includes equivalents thereof known to those skilled in the art. Additionally, the term "comprises" is intended to include embodiments where the method, apparatus, composition, etc., consists essentially of and/or consists of the listed steps, components, etc. Similarly, the term "consists essentially of" is intended to include embodiments where the method, apparatus, composition, etc., consists of the listed steps, components, etc.

As used herein, the term "about" refers to a number that differs from the given number by less than 10%. In certain embodiments, the term "about" indicates that the number differs from the given number by less than 9%, 8%, 7%, 6%, 5%, 4%, 3%, 2%, or 1%.

As used herein, the term "hairy root" refers to the structure which is formed as a consequence of the interaction between Agrobacterium rhizogenes and a host plant. Hairy roots are capable of unlimited growth and can be genetically engineered to express a nucleotide sequence of interest.

As used herein, the term "isolated" refers to a protein, polypeptide, peptide, nucleic acid molecule, polynucleotide, host cell, or virus that is removed from its natural environment (i.e., separated from at least one other component(s) with which it is naturally associated).

As used herein, the term "sequence identity" refers to the percent identity between two polypeptides or between two polynucleotides. The percent identity between two polypeptides is a function of the number of identical positions shared by the sequences, taking into account the number of gaps which need to be introduced for optimal alignment and the length of each gap. Various computer programs and mathematical algorithms are available in the art to determine the percentage of identity between amino acid sequences, such as for example the Blast program (e.g. Altschul et al., 1997, Nucleic Acid Res. 25:3389; Altschul et al., 2005, FEBS J. 272:5101) available at NCBI. The same can be applied for nucleotide sequences. Programs for determining nucleotide sequence homology are also available in specialized data base (Genbank or the Wisconsin Sequence Analysis Package), for example BLASTN, BESTFIT, FASTA and GAP programs.

The present invention pertains to extracts of a Morinda species, such as the Morinda officinalis How (MO) plant. The present invention also pertains to methods of treating an inflammatory bowel disease in a subject comprising administering to the subject an effective amount of an extract of a MO plant. In some embodiments, the extract of the MO plant is from the hairy root of the MO plant. In other embodiments, the extract of the MO plant comprises iridoid and anthraquinone.

In some embodiments, the iridoid is between about 0.20% and 5.0% of the dry weight of the extract. In other embodiments, the iridoid is between about 0.50% and 4.50%, between about 1.0% and 4.0%, between about 1.5% and 3.5%, or between about 2.0% and 3.0% of the dry weight of the extract. In other embodiments, the iridoid is between about 0.20% and 0.5%, 1.0%, 1.5%, 2.0%, 2.5% 3.0%, 3.5%, 4.0%, or 4.5% of the dry weight of the extract. In further embodiments, the iridoid is about 0.20%, 0.50%, 0.75%, 1.0%, 1.25%, 1.5%, 1.75%, 2.0%, 2.25%, 2.5%, 2.75%, 3.0%, 3.25%, 3.5%, 3.75%, 4.0%, 4.25%, 4.5%, 4.75%, or 5.0% of the dry weight of the extract.

In some embodiments, the iridoid comprises monotropein and deacetylasperulosidic acid. In further embodiments the monotropein is between about 0.25% and 2.5% of the dry weight of the extract. In yet other embodiments, the monotropein is between about 0.50% and 2.0%, between about 0.75% and 1.5%, or between about 1.0% and 1.25% of the dry weight of the extract. In other embodiments, the monotropein is between about 0.20% and 0.5%, 1.0%, 1.5%, 2.0%, or 2.5% of the dry weight of the extract. In some embodiments, the monotropein is about 0.25%, 0.50%, 0.75%, 1.0%, 1.25%, 1.5%, 1.75%, 2.0%, 2.25%, or 2.5% of the dry weight of the extract. In other embodiments, the deacetylasperulosidic acid is between about 0.1% and 2.0% of the dry weight of the extract. In yet other embodiments, the deacetylasperulosidic acid is between about 0.25% and 1.75%, between about 0.50% and 1.50%, or between about 0.75% and 1.25% of the dry weight of the extract. In further embodiments, the deacetylasperulosidic acid is between about 0.1% and 0.25%, 0.5%, 1.0%, 1.5%, or 2.0% of the dry weight of the extract. In yet other embodiments, the deacetylasperulosidic acid is about 0.1%, 0.15%, 0.20%, 0.25%, 0.30%, 0.35%, 0.40%, 0.45%, 0.50%, 0.55%, 0.60%, 0.65%, 0.70%, 0.75%, 0.80%, 0.85%, 0.90%, 1.0%, 1.05%, 1.10%, 1.15%, 1.20%, 1.25%, 1.30%, 1.35%, 1.40%, 1.45%, 1.50%, 1.55%, 1.60%, 1.65%, 1.70%, or 1.75% of the dry weight of the extract.

In yet other embodiments, the anthraquinone is less than about 1.0% of the dry weight of the extract. In some other embodiments, the anthraquinone is about 1.0% of the dry weight of the extract. In other embodiments, the anthraquinone is less than 0.95%, 0.90%, 0.85%, 0.80%, 0.75%, 0.70%, 0.65%, 0.60%, 0.55%, 0.50%, 0.45%, 0.40%, 0.35%, 0.30%, 0.25%, 0.20%, 0.15%, 0.10%, or 0.05% of the dry weight of the extract. In further embodiments, the anthraquinone is less than about than 0.95%, 0.90%, 0.85%, 0.80%, 0.75%, 0.70%, 0.65%, 0.60%, 0.55%, 0.50%, 0.45%, 0.40%, 0.35%, 0.30%, 0.25%, 0.20%, 0.15%, 0.10%, or 0.05% of the dry weight of the extract. In yet other embodiments, the anthraquinone is between about 0.01% and 1.0% of the dry weight of the extract. In some other embodiments, the anthraquinone is between about 0.10% and 0.90%, between about 0.20% and 0.80%, between about 0.30% and 0.70%, or between about 0.40% and 0.50% of the dry weight of the extract.

In some embodiments, the anthraquinone comprises rubiadin-1-methyl ether. In further embodiments, the rubiadin-1-methyl ether is less than about 0.15% of the dry weight of the extract. In yet other embodiments, the rubiadin-1-methyl ether is less than about 0.1% of the dry weight of the extract. In other embodiments, the rubiadin-1-methyl ether is about 0.15% of the dry weight of the extract. In still other embodiments, the rubiadin-1-methyl ether is about 0.1% of the dry weight of the extract. In yet other embodiments, the rubiadin-1-methyl ether is between about 0.001% and 0.15%, between about 0.01% and 0.15%, or between about 0.10% and 0.15% of the dry weight of the extract.

The present invention also pertains to an isolated nucleic acid molecule comprising a nucleotide sequence having at least 80%, 85%, 90%, 95%, or 100% sequence identity to the cDNA nucleotide sequence of SEQ ID NO:1. In other embodiments, the isolated nucleic acid molecule comprises a nucleotide sequence having at least 80%, 81%, 82%, 83%, 84%, 85%, 86%, 87%, 88%, 89%, 91%, 92%, 93%, 94%, 96%, 97%, 98%, or 99% sequence identity to the cDNA nucleotide sequence of SEQ ID NO:1.

The present invention also pertains to a polypeptide sequence which is encoded by a nucleotide sequence having at least 80%, 85%, 90%, 95%, or 100% sequence identity to the cDNA nucleotide sequence of SEQ ID NO:1. In further embodiments, the polypeptide sequence is encoded by a nucleotide sequence having at least 91%, 92%, 93%, 94%, 96%, 97%, 98%, or 99% sequence identity to the cDNA nucleotide sequence of SEQ ID NO:1. The present invention also pertains to a nucleotide sequence encoding an amino acid sequence having at least 80%, 85%, 90%, 95%, or 100% sequence identity to the amino acid sequence of SEQ ID NO:2. In further embodiments, the nucleotide sequence encodes an amino acid sequence having at least 91%, 92%, 93%, 94%, 96%, 97%, 98%, or 99% sequence identity to the amino acid sequence of SEQ ID NO:2. The invention also pertains to a polypeptide comprising an amino acid sequence encoding chalcone synthase that has at least 80%, 85%, 90%, 91%, 92%, 93%, 94%, 95%, 96%, 97%, 98%, 99% or 100% sequence identity to the amino acid sequence of SEQ ID NO:2.

The present invention also pertains to an expression vector comprising a nucleotide sequence encoding a chalcone synthase polypeptide. In some embodiments, the chalcone synthase polypeptide is from *Eucalyptus camaldulensis*. In further embodiments, the expression vector comprising a nucleotide sequence having at least 80%, 85%, 90%, 95%, or 100% sequence identity to the cDNA nucleotide sequence of SEQ ID NO:1. In other embodiments, the expression vector comprises a nucleotide sequence having at least 80%, 81%, 82%, 83%, 84%, 85%, 86%, 87%, 88%, 89%, 91%, 92%, 93%, 94%, 96%, 97%, 98%, or 99% sequence identity to the cDNA nucleotide sequence of SEQ ID NO:1. In another embodiment, the expression vector comprises a nucleotide sequence encoding a polypeptide having chalcone synthase activity and comprising an amino acid sequence that has at least 80%, 85%, 90%, 91%, 92%, 93%, 94%, 95%, 96%, 97%, 98%, 99% or 100% sequence identity to the amino acid sequence of SEQ ID NO:2. In yet other embodiments, the expression vector further comprises a promoter, wherein the promoter is not endogenous to *Eucalyptus camaldulensis*. Examples of suitable promoters are cauliflower mosaic virus 19S and 35 S promoters.

The present invention also pertains to an *Agrobacterium rhizogenes* bacterium comprising an expression vector comprising a nucleotide sequence encoding a chalcone synthase polypeptide. In some embodiments, the chalcone synthase polypeptide is from *Eucalyptus camaldulensis*. In further embodiments, the nucleotide sequence has at least 80%, 85%, 90%, 95%, or 100% sequence identity to the cDNA nucleotide sequence of SEQ ID NO:1. In other embodiments, said nucleotide sequence has at least 80%, 81%, 82%, 83%, 84%, 85%, 86%, 87%, 88%, 89%, 91%, 92%, 93%, 94%, 96%, 97%, 98%, or 99% sequence identity to the cDNA nucleotide sequence of SEQ ID NO:1 and encodes a polypeptide having chalcone synthase activity. In another embodiment, the nucleotide sequence encodes a polypeptide having chalcone synthase activity and comprising an amino acid sequence that has at least 80%, 85%, 90%, 91%, 92%, 93%, 94%, 95%, 96%, 97%, 98%, 99% or 100% sequence identity to the amino acid sequence of SEQ ID NO:2.

The present invention also pertains to a plant or plant part from the family of *Morinda*, preferably a MO plant or plant part, transformed by an *Agrobacterium rhizogenes* bacterium comprising an expression vector comprising a nucleotide sequence encoding a chalcone synthase polypeptide. In some embodiments, the chalcone synthase polypeptide is from *Eucalyptus camaldulensis*. In further embodiments, the nucleotide sequence has at least 80%, 85%, 90%, 95%, or 100% sequence identity to the cDNA nucleotide sequence of SEQ ID NO:1. In other embodiments, said nucleotide sequence has at least 80%, 81%, 82%, 83%, 84%, 85%, 86%, 87%, 88%, 89%, 91%, 92%, 93%, 94%, 96%, 97%, 98%, or 99% sequence identity to the cDNA nucleotide sequence of SEQ ID NO:1. In another embodiment, the nucleotide sequence encodes a polypeptide having chalcone synthase activity and comprising an amino acid sequence that has at least 80%, 85%, 90%, 91%, 92%, 93%, 94%, 95%, 96%, 97%, 98%, 99% or 100% sequence identity to the amino acid sequence of SEQ ID NO:2.

The present invention also pertains to an extract of a MO plant transformed by an *Agrobacterium rhizogenes* bacterium, wherein the *Agrobacterium rhizogenes* bacterium comprises an expression vector, wherein the expression vector comprises a nucleotide sequence encoding a chalcone synthase polypeptide. In some embodiments, the nucleotide sequence has at least 80%, 85%, 90%, 95%, or 100% sequence identity to the cDNA nucleotide sequence of SEQ ID NO:1. In other embodiments, said nucleotide sequence has at least 80%, 81%, 82%, 83%, 84%, 85%, 86%, 87%, 88%, 89%, 91%, 92%, 93%, 94%, 96%, 97%, 98%, or 99% sequence identity to the cDNA nucleotide sequence of SEQ ID NO:1. In another embodiment, the nucleotide sequence encodes a polypeptide having chalcone synthase activity and comprising an amino acid sequence that has at least 80%, 85%, 90%, 91%, 92%, 93%, 94%, 95%, 96%, 97%, 98%, 99% or 100% sequence identity to the amino acid sequence of SEQ ID NO:2.

The present invention also pertains to methods of treating an inflammatory bowel disease in a subject comprising administering to the subject an effective amount of an extract of a MO plant. In one such method, an extract from an MO plant transformed by an *Agrobacterium rhizogenes* bacterium, wherein the *Agrobacterium rhizogenes* bacterium comprises an expression vector, wherein the expression vector comprises a nucleotide sequence encoding a chalcone synthase polypeptide, is administered at a therapeutically effective amount to a patient suffering from UC. In some embodiments, the nucleotide sequence has at least 80%, 85%, 90%, 95%, or 100% sequence identity to the cDNA nucleotide sequence of SEQ ID NO:1. In other embodiments, said nucleotide sequence has at least 80%, 81%, 82%, 83%, 84%, 85%, 86%, 87%, 88%, 89%, 91%, 92%, 93%, 94%, 96%, 97%, 98%, or 99% sequence identity to the cDNA nucleotide sequence of SEQ ID NO:1. In another embodiment, the nucleotide sequence encodes a polypeptide having chalcone synthase activity and comprising an amino acid sequence that has at least 80%, 85%, 90%, 91%, 92%, 93%, 94%, 95%, 96%, 97%, 98%, 99% or 100% sequence identity to the amino acid sequence of SEQ ID NO:2. In some embodiments, the extract is from the hairy root of said MO plant.

In other embodiments, the effective amount of an extract of a MO plant may be administered to the subject alone or as a pharmaceutical composition. The pharmaceutical composition may contain pharmaceutically acceptable excipients, such as vehicles, adjuvants, carriers or diluents, which are readily available to the public. Moreover, pharmaceutical compositions may also include pharmaceutically acceptable auxiliary substances, such as pH adjusting and buffering agents, tonicity adjusting agents, stabilizers, wetting agents and the like, which are readily available to the public. Details on techniques for formulation and administration are well described in the scientific and patent literature, see, for example, the latest edition of "Remington's Pharmaceutical Sciences" (Maack Publishing Co, Easton Pa.). In further embodiments, the compounds or pharmaceutical compositions of the present invention can be administered orally.

In further embodiments, the effective amount of an extract of a MO plant is administered to a human subject in the amount of between about 0.2 mg/kg to about 12 mg/kg. In another embodiment, the effective amount of an extract of a MO plant is administered to a human subject in the amount of between about 0.8 mg/kg to about 4 mg/kg. In other embodiments, the effective amount of an extract of a MO plant is administered to a human subject in the amount of about 0.2 mg/kg, 0.4 mg/kg, 0.6 mg/kg, 0.8 mg/kg, 1.0 mg/kg, 1.2 mg/kg, 1.4 mg/kg, 1.6 mg/kg, 1.8 mg/kg, 2.0 mg/kg, 2.2 mg/kg, 2.4 mg/kg, 2.6 mg/kg, 2.8 mg/kg, 3.0 mg/kg, 3.2 mg/kg, 3.4 mg/kg, 3.6 mg/kg, 3.8 mg/kg, 4.0 mg/kg, 4.2 mg/kg, 4.4 mg/kg, 4.6 mg/kg, 4.8 mg/kg, 5.0 mg/kg, 5.5 mg/kg, 6.0 mg/kg, 6.5 mg/kg, 7.0 mg/kg, 7.5 mg/kg, 8.0 mg/kg, 8.5 mg/kg, 9.0 mg/kg, 9.5 mg/kg, 10 mg/kg, 10.5 mg/kg, 11 mg/kg, 11.5 mg/kg, or 12 mg/kg. In yet other embodiments, the effective amount of an extract of a MO plant is administered to a human subject in the amount of more than about 0.2 mg/kg, 0.4 mg/kg, 0.6 mg/kg, or 0.8 mg/kg. In other embodiments, the effective amount of an extract of a MO plant is administered to a human subject in the amount of less than 4.0 mg/kg, 4.2 mg/kg, 4.4 mg/kg, 4.6 mg/kg, 4.8 mg/kg, 5.0 mg/kg, 5.5 mg/kg, 6.0 mg/kg, 6.5 mg/kg, 7.0 mg/kg, 7.5 mg/kg, 8.0 mg/kg, 8.5 mg/kg, 9.0 mg/kg, 9.5 mg/kg, 10 mg/kg, 10.5 mg/kg, 11 mg/kg, 11.5 mg/kg, or 12 mg/kg. In further embodiments, the effective amount of an extract of a MO plant is administered to a human subject in the amount of between about 0.2 mg/kg to about 11.5 mg/kg, between about 0.2 mg/kg to about 11.0 mg/kg, between about 0.4 mg/kg to about 10.5 mg/kg, between about 0.4 mg/kg to about 10 mg/kg, between about 0.4 mg/kg to about 9.5 mg/kg, between about 0.4 mg/kg to about 9 mg/kg, between about 0.4 mg/kg to about 8.5 mg/kg, between about 0.4 mg/kg to about 8.0 mg/kg, between about 0.4 mg/kg to about 7.5 mg/kg, between about 0.4 mg/kg to about 7 mg/kg, between about 0.4 mg/kg to about 6.5 mg/kg, between about 0.4 mg/kg to about 6.0 mg/kg, between about 0.4 mg/kg to about 5.5 mg/kg, between about 0.4 mg/kg to about 5.0 mg/kg, between about 0.4 mg/kg to about 4.8 mg/kg, between about 0.4 mg/kg to about 4.6 mg/kg, between about 0.4 mg/kg to about 4.4 mg/kg, between about 0.4 mg/kg to about 4.2 mg/kg, between about 0.6 mg/kg to about 4.0 mg/kg, between about 0.6 mg/kg to about 3.8 mg/kg, between about 0.6 mg/kg to about 3.6 mg/kg, between about 0.6 mg/kg to about 3.4 mg/kg, between about 0.6 mg/kg to about 3.2 mg/kg, between about 0.6 mg/kg to about 3.0 mg/kg, between about 0.6 mg/kg to about 2.8 mg/kg, between about 0.8 mg/kg to about 3.8 mg/kg, between about 0.8 mg/kg to about 3.6 mg/kg, between about 0.8 mg/kg to about 3.4 mg/kg, between about 0.8 mg/kg to about 3.2 mg/kg, between about 0.8 mg/kg to about 3.0 mg/kg, between about 0.8 mg/kg to about 2.8 mg/kg, between about 0.8 mg/kg to about 2.6 mg/kg, between about 1.2 mg/kg to about 4.2 mg/kg, between about 1.2 mg/kg to about 4.0 mg/kg, between about 1.2 mg/kg to about 3.8 mg/kg, between about 1.2 mg/kg to about 3.6 mg/kg, between about 1.2 mg/kg to about 3.4 mg/kg, between about 1.2 mg/kg to about 3.2 mg/kg, between about 1.2 mg/kg to about 3.0 mg/kg, between about 1.2 mg/kg to about 2.8 mg/kg, between about 1.2 mg/kg to about 2.6 mg/kg, between about 1.6 mg/kg to about 4.2 mg/kg, between about 1.6 mg/kg to about 4.0 mg/kg, between about 1.6 mg/kg to about 3.8 mg/kg, between about 1.6 mg/kg to about 3.6 mg/kg, between about 1.6 mg/kg to about 3.4 mg/kg, between about 1.6 mg/kg to about 3.2 mg/kg, between about 1.6 mg/kg to about 3.0 mg/kg, between about 1.6 mg/kg to about 2.8 mg/kg, or between about 1.6 mg/kg to about 2.6 mg/kg.

Figure 9A:
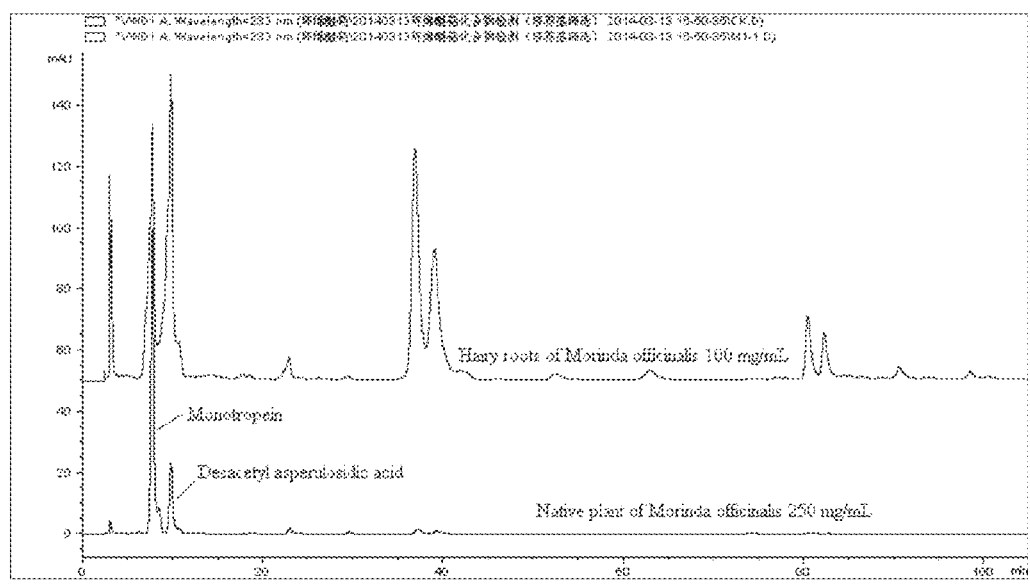
FIGS. 9A and 9B depict the HPLC profiles of extracted MO hairy roots.
Figure 9B:
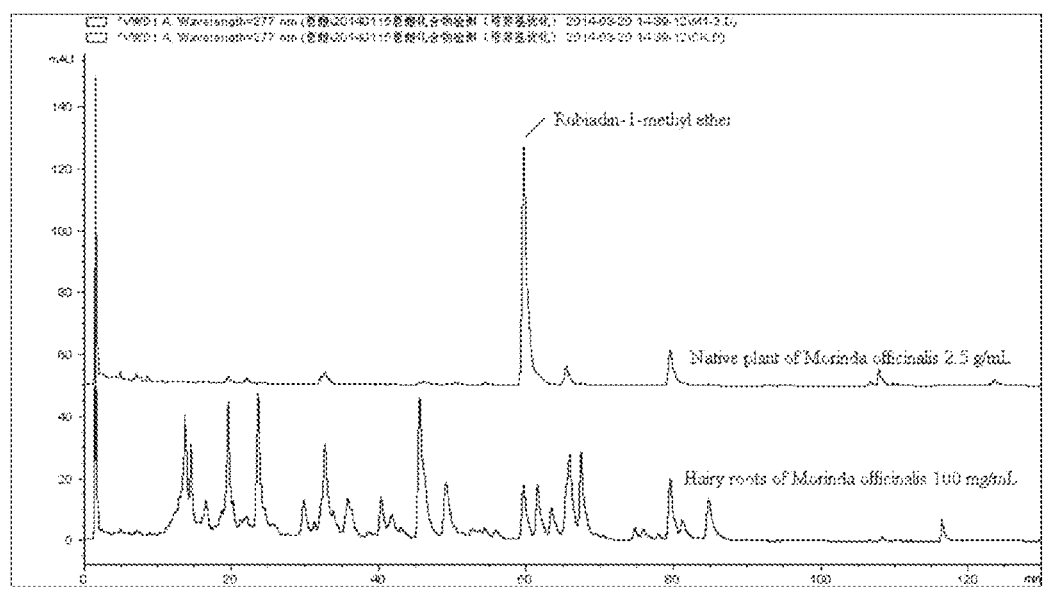

In further embodiments, the extract of the hairy roots of the MO plant comprises the one or more specific chemicals identified by novel peaks depicted in the HPLC profiles of methanolic extract of MO hairy roots, as shown in FIG. 9A-B. In other embodiments, the extract of the MO plant comprises one or more of the chemicals identified at the 80 minute peaks at wavelength 223 nm (FIG. 9A). In still other embodiments, the extract of the MO plant comprises one or more of the chemicals identified at peaks at 15 to 20 minutes of wavelength 277 nm (FIG. 9B). In yet another embodiment, the extract of the MO plant comprises one or more of the chemicals identified at the peaks at 20 to 40 minutes of wavelength 277 nm (FIG. 9B).

In another embodiment, disclosed is a method of generating increased levels of metabolites in hairy roots of the *Morinda* species by transfecting plants or plant parts, such as plantlets, with *A. rhizogenes* which contain an expression vector carrying cDNA encoding a chalcone synthase and selecting for hairy root clones which were transformed with the nucleotides encoding for the chalcone synthase polypeptide. In this embodiment, higher production of desirable metabolites is produced in roots. Suitable Morinda species include MO, *Morinda citrifolio, Morinda lucida, Morinda elliptica, Morinda pandurifolia*, and *Morinda angustifolia*. Pistelli, L. et al. (2010) provides a review of aspects of hairy root induction, genetics and metabolite production that is useful to practice the inventive methods of genetic transformation.

Hairy root disease can be caused by *Agrobacterium rhizogenes*, which can be isolated from the soil. The gram-negative bacterium transfers DNA from its root-inducing (Ri) plasmid into the genome of the infected plant cell which results in the formation of roots. Its use in the control of beneficial growth of roots was described by Strobel, U.S. Pat. No. 4,588,693. In the production of hairy root cultures, the plant is infected with the *Agrobacterium* by exposure of plant cells or plant parts to *Agrobacterium*. Any plant part, tissue or cell capable of producing hairy roots can be used in the invention. Such plant parts can include, for example and without limitation, plant stem, petiole, cotyledonary node, hypocotyl, or other plant parts or cells. A semi-solid medium or liquid nutrient solution is preferably employed which is optimized for maintenance of roots, resulting in increased growth rate of roots compared to non-infected plant cells. While many types of material and solutions and medium are known and can be used in the invention, several preferred examples include Murashige and Skoog and Gamborg B5 medium. Several media modifications optimized for meeting in vitro nutrient requirements of different host plants used in making sustainable hairy root cultures can be employed.

EXAMPLES

Example 1

Cloning of a Chalcone Synthase (CHS) cDNA and Vector Construction

Freshly collected red eucalyptus (*Eucalyptus camaldulensis*) leaves were frozen in liquid nitrogen and stored at −80° C. RNA was isolated with a RNA extraction kit (Clontech, Palo Alto, USA) according to manufacturer's instructions.

mRNA was purified from total RNA using a Magnosphere Ultrapure mRNA Purifition Kit (Clontech, Palo Alto, USA). cDNA was synthesized from mRNA using a cDNA synthesis kit from Clontech. Full length cDNA coding for chalcone synthase was amplified from the cDNA pool by PCR (polymerase chain reaction) using primers EcCHSF1 (ATGGTGAGCGTCGAGGAATT) (SEQ ID NO:3) and EcCHSR1 (TTAAGCAGACAGGGCGTGGA) (SEQ ID NO: 4). The resulting cDNA is created from mRNA, which does not include the genomic introns. The *E. camaldulensis* CHS gene comprises at least two exons with an intervening intron. The PCR conditions were as follows: 95 C for 10 min, then 30 cycles of 95 C for 30 s, 58 C for 30 s, 72 C for 1,5 min, and 72 C for 5 min. CHS DNA was purified after agarose electrophoresis using a DNA Purification kit from Clontech, cloned into pMD-19T (Clontech), and sequenced.

Figure 4:
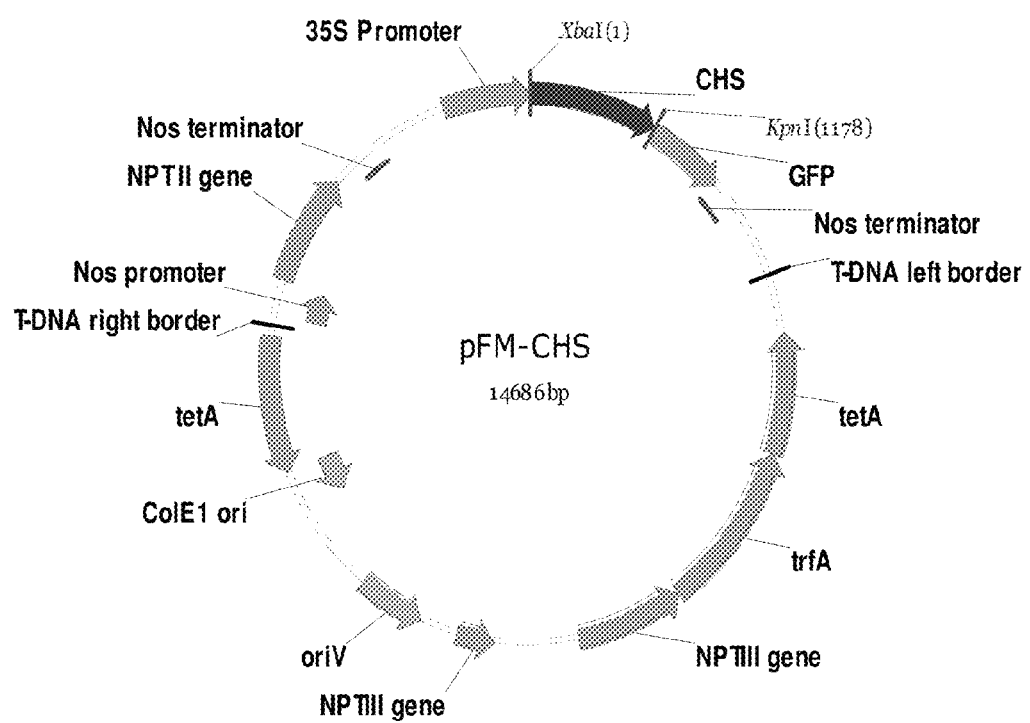
FIG. 4 depicts the plasmid map of pFM-CHS.
Figure 5A:
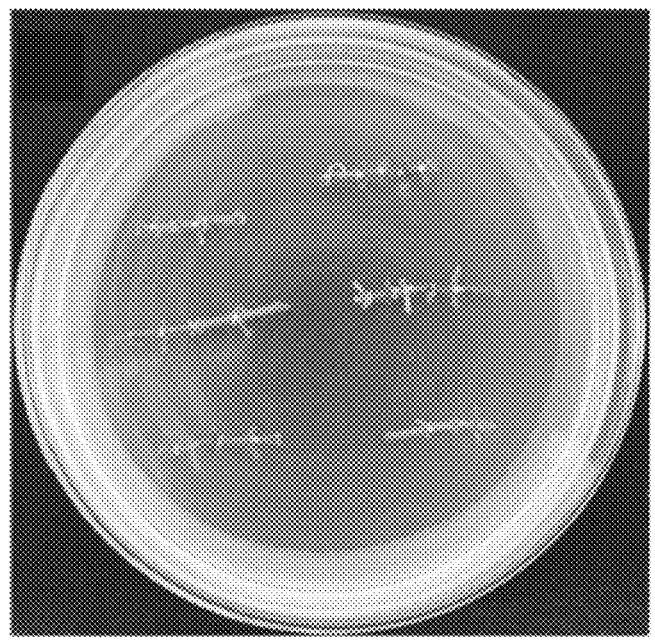
FIG. 5 A-D shows various stages of aseptic growth of explants. It takes about 6-8 week to reach stage D (FIG. 5D) from stage A (FIG. 5A).
FIG. 5E represents young plantlets which are ready for transfection.
Figure 5B:
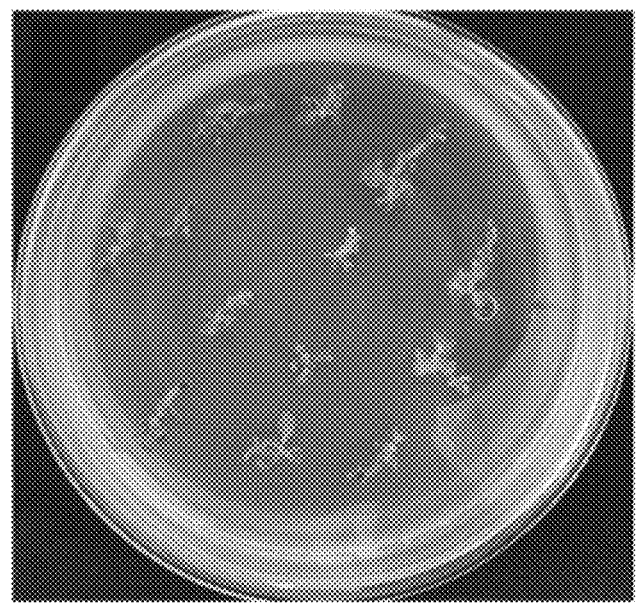
Figure 5C:
Figure 5D:
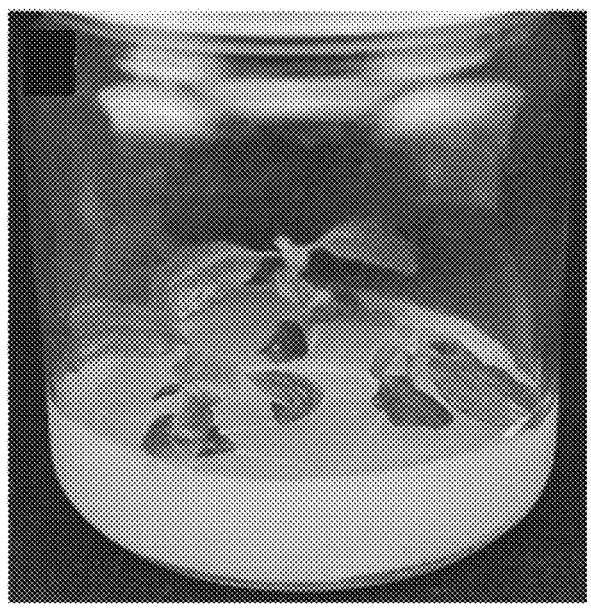
Figure 5E:
Figure 6A:
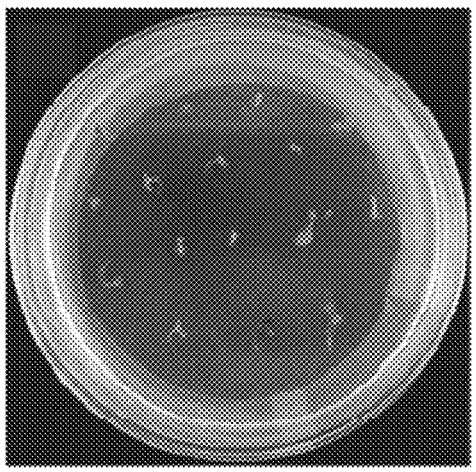
FIG. 6A-F depicts the process of induction of hairy roots.
Figure 6B:
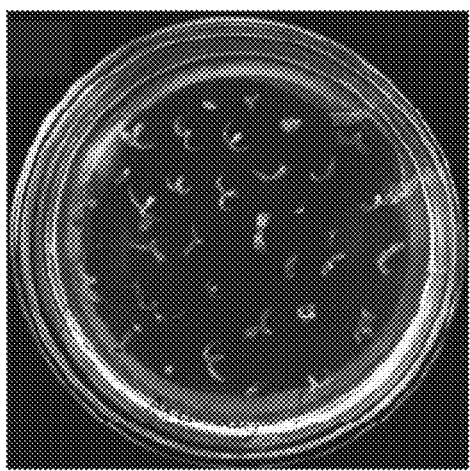
Figure 6C:
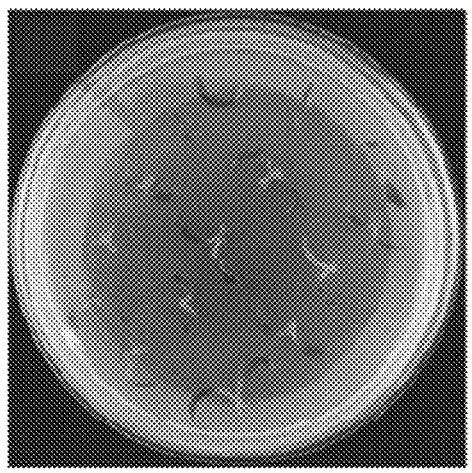
Figure 6D:
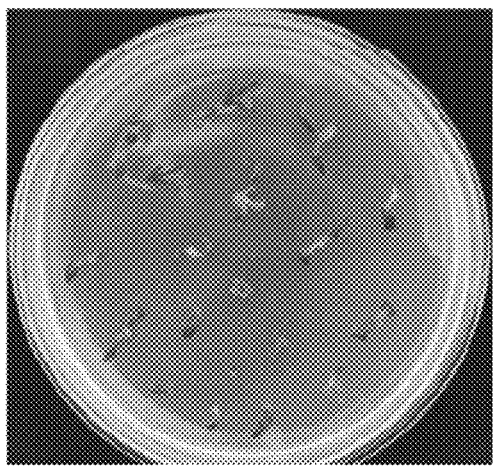
Figure 6E:
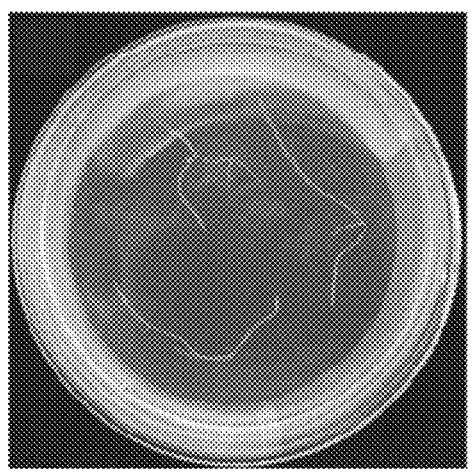
Figure 6F:
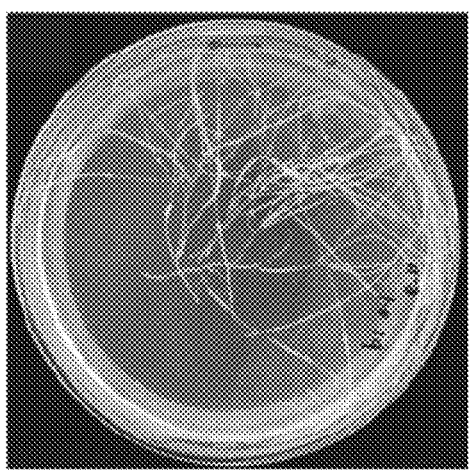

Sequencing results revealed a cDNA of 1170 by (FIG. 3A) with an open reading frame translated to 390 amino acids (FIG. 3B). An expression vector was then constructed by cloning the CHS DNA under the transcriptional control of the *Cauliflower mosaic* virus 35S promoter in pRI 101-AN (Clontech), a binary plant expression vector. This vector was named pFM-CHS (FIG. 4) and used in all transfection studies to generate transgenic plants.

Example 2

Transformation of MO Using *Agrobacterium rhizogenes*

A. Micropropagation of Plantlets

Young shoots of MO were excised from adult plants, trimmed, and cut into 1-cm sections, washed with distilled water for 1 hour, 75% ethyl alcohol for 50 sec, and 0.1% mercurochrome for 10 min. The explants were then rinsed 3 times in distilled water, air-dried, and placed on ½ strength Murashige and Skoog (MS) medium supplemented with 300 mg/l Cefotaxime until aseptic culture was established. The decontaminated shoots were then cultured on solid medium containing ½ MS, IBA (2.0 mg/l), and sucrose (15%). After 2 months growth, the aseptic plantlets were trimmed of leaves and cut into 0.5-1.5 cm sections (FIG. 5A-E) and cultured on ½ MS medium for 3-5 days before transfecting with *Agrobacterium rhizogenes*.

B. Establishment of Hairy Root Clones

*Agrobacterium rhizogenes* ATCC 15834 transformed with pFM-CHS was grown in 10 ml YEB medium overnight at 28 C with shaking at 200 rpm to an OD600 of 0.5-0.8. The culture was then centrifuged and the cells resuspended in ½ MS medium and adjusted to OD600 of 0.6.

Young plantlets from culture stock (FIG. 5 E) were trimmed of leaves and roots and cut into 1-cm sections and sonicated in ½ MS liquid medium at room temperature for 5 min, and then immersed in *A. rhizogenes* culture for 15 min, blotted dry, transferred to culture medium (½ MS+100 uM acetosyringone, and grown for 3-5 days. The transfected explants were then transferred to decontaminating medium (1× MS+cefotaxime 300 mg/l) and subcultured every 5-10 days (FIG. 6 A, B). After 3-4 weeks, hairy roots appeared at the cut ends of the explants (FIG. 6 A-F). Hairy roots were picked when reached 2 cm in length, and subcultured every 3-4 weeks. The rapidly growing clones without bacterial contamination were selected for PCR analysis to confirm successful transformation. These transfection conditions were the results of 12 optimization experiments involving 4280 explants with a cloning efficiency of 3.2%.

C. Identification of Clones Using PCR

Figure 7:
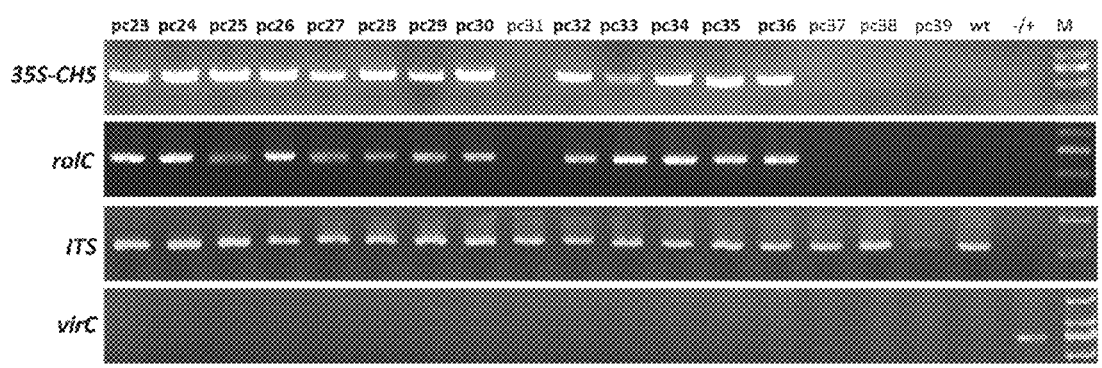
FIG. 7 shows an agarose gel electrophoresis of PCR products amplified from MO genomic DNA isolated from transgenic hairy root clones using various primers specific for CHS, rolC, ITS and virC.

The transformed root clones were confirmed by PCR using primers specific for CHS, and T-DNA. The size of the PCR products indicated that the CHS gene was integrated into the genome of MO (FIG. 7). The absence of PCR products for virC indicated that the positive amplification for roIC and CHS is not due to residual *A. rhizogenes*. PCR product for internal transcribed spacer (ITS) was used as a DNA quality control. The clones were analyzed for iridoid and anthraquinone productivity by HPLC analysis after 6 weeks of growth in MS medium.

D. Productivity of Hairy Root Clones

Figure 8:
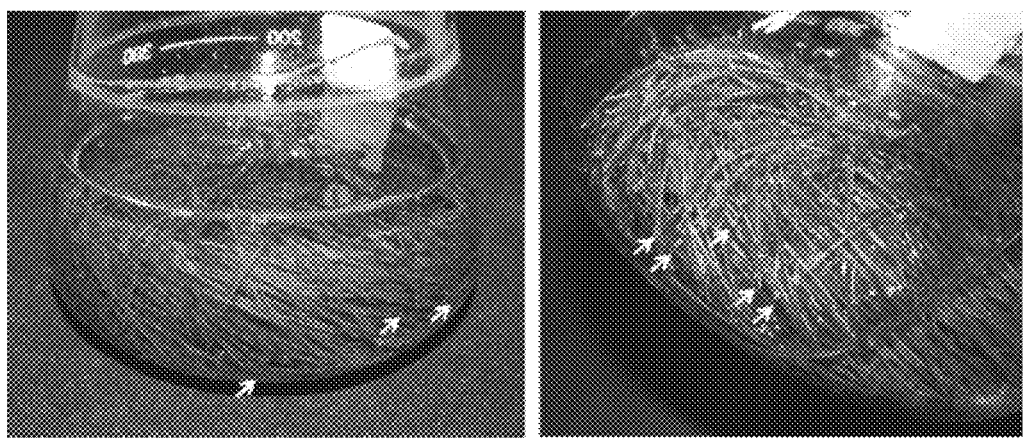
FIG. 8 depicts a shake flask culture of hairy root clones at the end of 60-day growth. Arrows indicate thickened regions.

The productivity of the transgenic hairy root clones was evaluated in 500-ml Erlenmeyer flasks (FIG. 8). 0.5 g hairy roots were inoculated into 300 ml of ½ MS medium and grown for 60 days at 25 C in a shaker platform at 100 rpm. At the end of the growth period, the hairy roots were harvested, dried at 50 C in an oven until constant weight was achieved, extracted with methanol, and analyzed by reversed-phase HPLC as described in Example 3 for anthraquinones and iridoids. As shown in Table 1, the anthraquinone productivity of all the hairy root clones is significantly higher (50-90 fold) than the native plant while iridoid productivity varies from lower to marginally higher.

TABLE 1

Productivity of hairy root clones grown in shake flasks for 60 days

| Sample | Anthraquinone mg/g | Iridoid mg/g |
|---|---|---|
| Native plant | 0.03 | 14.9 |
| Clone C1 | 2.83 | 21.9 |
| C2 | 3.68 | 33.8 |
| C3 | 2.72 | 6.3 |
| C4 | 1.54 | 4.2 |
| C5 | 2.03 | 3.3 |
| C6 | 1.24 | 17.2 |
| C7 | 2.44 | 29.5 |
| C8 | 0.74 | 26.7 |
| C9 | 1.04 | 17.4 |
| C10 | 2.3 | 11.7 |
| C11 | 1.03 | 13.6 |

Example 3

HPLC Profile of Iridoid and Anthraquinones Extracted from Hairy Roots

Dried powdered roots (4 kg) and hairy roots (288 g) were extracted with methanol two times under reflux. The extract was then filtered and evaporated under reduced pressure. The concentrated extract was freeze-dried and resuspended in water prior to analysis or used in animal studies. The yield was 13.77% for native roots and 34.38% for hairy roots.

Methanolic extracts of various hairy root clones and native herb were analyzed by reverse phase HPLC to quantitate the levels of iridoids and anthraquinones on a C18 column. Purified monotropein and rubiadin-1-methyl ether were used to generate standard curves.

As shown in FIG. 9 A, the iridoid profile of extracts from transgenic hairy roots of MO is similar to the native plant but at higher concentrations. Both monotropein and deacetylasperulosidic acid peaks were prominently detected. Due to the drastic increase in concentrations of anthraquinones in hairy roots, the HPLC profile (FIG. 9 B) is quite different than the native plant whereas rubiadin-1-methyl ether is the major component.

Example 4

Animal Model for Ulcerative Colitis

The therapeutic efficacy of the methanolic extracts of MO hairy roots was examined in an acute mouse ulcerative colitis model. The mouse ulcerative colitis model is used to predict ulcerative colitis and treatment of that disease in human subjects (e.g. Low et. al., 2013). Male BalbC mice in groups of 10 were housed in Good Animal Care Protocol conditions. Colitis was induced by 4% dextran sulfate (DSS). In a pilot dosing study (50 mg/kg, 150 mg/kg, and 450 mg/kg) of MO root extracts on UC, an unexpected finding was made. There are no beneficial effects on UC at extract concentrations above 50 mg/kg.

Subsequently the effect of drug treatment on colitis was investigated by co-feeding the mice extracts from MO native plants or hairy root culture at doses below 50 mg/kg along with 4% DSS for 7 days. 5-amino-salicylic acid (5-ASA) was used as a positive treatment control. Animals were weighed, and stool consistency was monitored daily to determine the disease activity index (DAI. All animals were anesthetized and the colons were separated from the proximal rectum, and the colon length was measured between the ileo-cecal junction and the proximal rectum.

TABLE 2

Evaluation of DAI scores

| DAI Score | Weight loss (%) | Stool consistency | Bleeding* |
|---|---|---|---|
| 0 | None | Normal | No bleeding |
| 1 | 1-5 | Soft stool | Faint blue |
| 2 | 5-10 | Soft to loose stool | Diffused blue |
| 3 | 10-20 | Loose stool | Distinct blue |
| 4 | >20 | Diarrhea | Gross bleeding |

*Hemoccult test. Blue color indicates presence of blood in stool

TABLE 3

Treatment of DSS-induced ulcerative colitis in mouse with extracts from *Morinda officinalis* native plants and transgenic hairy roots

| | DAI | Length of colon (cm) | % of mice developing ulcer# |
|---|---|---|---|
| Normal (water only) | 0.1 ± 0.16 | 7.64 ± 0.34 | 0 |
| DSS only | 6.6 ± 3.81## | 5.88 ± 0.23## | 80 |
| 5-ASA 20 mg/kg | 3.0 ± 2.22** | 6.77 ± 0.19* | 60 |
| Native plant 40 mg/kg | 3.0 ± 2.92** | 6.31 ± 0.21 | 30 |
| Native plant 20 mg/kg | 2.7 ± 1.74** | 6.78 ± 0.19* | 20 |
| Native plant 10 mg/kg | 3.2 ± 2.43** | 6.19 ± 0.38 | 30 |
| Hairy root 40 mg/kg | 3.1 ± 2.07** | 6.70 ± 0.17* | 10 |
| Hairy root 20 mg/kg | 2.6 ± 1.44** | 7.06 ± 0.35** | 10 |
| Hairy root 10 mg/kg | 3.3 ± 2.17** | 6.13 ± 0.22 | 20 |

Compare to DSS only **$P < 0.01$, *$P < 0.05$;
Compare to normal group (water only) ##$P < 0.01$.
DAI = Disease activity index
Including disruption of colonic crypts and damaged glandular structures As shown in Table 3, following induction of colitis, the combinatorial DAI scores, which incorporate body weight loss, stool consistency, and gross bleeding, were significantly increased in the DSS-only (UC model) group. Over 90% of the animals had bloody stools. The intestines were relatively easy to break and associated with hyperemia and abscess. 50% of the animals had serious ulcers and adhesions. The length of the colon was also significantly reduced. The administration of extracts from both the native plant and the hairy roots were able to significantly reduce the DAI score. The length of the colon of the drug treated mice was significantly increased, indicating therapeutic effects on colitis when compared to 5-ASA treated mice.

Histopathology examination of the colon from the 5 groups of mice revealed that the number of animals with development of ulcers and destruction of intestinal linings is significantly lower in the groups treated with extracts from the hairy roots and native plants when compared to the 5-ASA group. The groups of mice treated with extracts from MO hairy roots were also found to have the lowest incidence of ulcers, indicating improved therapeutic efficacy versus the groups treated with 5-ASA or extracts from the native plant.

The high potency of the hairy root extract was confirmed in 3 separate studies and the iridoid and anthraquinone contents measured by HPLC (Table 4).

TABLE 4

Major constituents of hairy root extracts

| Constituents of Hairy Root used in animal studies | Range of % Dry Weight |
|---|---|
| Total anthraquinones | 0.001-1.0% |
| Rubiadin-1-methyl ether | 0.001-0.15% |
| Total iridoids | 0.2-5.0% |
| Monotropein | 0.25-2.5% |
| Deacetylasperulosidic acid | 0.1-2.0% |

REFERENCES

Bao, L. and L. Qin, et al. (2011). "Anthraquinone compounds from *Morinda officinalis* inhibit osteoclastic bone resorption in vitro." Chemico-Biological Interactions 194 (2-3): 97-105.

Choi, J. and K. T. Lee, et al. (2005). "Antinociceptive anti-inflammatory effect of Monotropein isolated from the root of Morinda officinalis." Biol Pharm Bull 28 (10): 1915-8.

Ke, F., Yadav, P. K., and Ju, L. Z. (2012). "Herbal Medicine in the Treatment of Ulcerative Colitis." Saudi J Gastroenterol 18: 3-10.

Li, N., Qin, L. P., et al. (2009). "Inhibitory Effects of *Morinda officinalis* Extract on Bone Loss in Ovariectomized Rats." Molecules 14: 2049-2061.

Low, D, Nguyen, D D, and Mizoguchi, E. (2013). "Animal models of ulcerative colitis and their application in drug research." Drug Design, Development and Therapy 7: 1341-1357.

Palladino, M. A., et al. (2003). "Anti-TNF-a Therapies: The Next Generation." Nature Reviews 2: 736-746.

Pistelli, L., Giovannini, A., Ruffoni, B., Bertoli, A., and Pistelli, L. (2010). "Hairy Root Cultures for Secondary Metabolites Production." *Bio-Farms for Nutraceuticals: Functional Food and Safety Control by Biosensors*. Chapter 13: 168-184.

Ruoyi, Z. (2010). "Protective effects of polysaccharides extracted from Morinda Officinalis on fetal rat hippocampal neurons." Hong Kong, The University of Hong Kong. Master.

Samaan, M. A. and P. Bagi, et al. (2014). "An Update on Anti-TNF Agents in Ulcerative Colitis." Gastroenterology Clinics of North America 43 (3): 479-494.

Shin, J. and K. Yun, et al. (2013). "Monotropein isolated from the roots of *Morinda officinalis* ameliorates proinflammatory mediators in RAW 264.7 macrophages and dextran sulfate sodium (DSS)-induced colitis via NF-?B inactivation." Food and Chemical Toxicology 53: 263-271.

Soon, Y. Y. and B. K. Tan (2002). "Evaluation of the hypoglycemic and anti-oxidant activities of Morinda officinalis in streptozotocin-induced diabetic rats." Singapore Med J 43 (2): 077-85.

Wu, Y. B., Zheng, C. J., Qin, L. P., et al. (2009). "Antiosteoporotic Activity of Anthraquinones from *Morinda officinalis* on Osteoblasts and Osteoclasts." Molecules 14: 573-583.

YOSHIKAWA, M. and S. YAMAGUCHI, et al. (1996). "ChemInform Abstract: Chemical Constituents of Chinese Natural Medicine, Morindae Radix, the Dried Roots of *Morinda officinalis* How.: Structures of Morindolide and Morofficinaloside." ChemInform 27 (12): no-no.

Zhou, M., Zhu, X., Shao, J., Tang, Y., and Wu, Y. (2011). "Production and metabolic engineering of bioactive substances in plant hairy root culture." Appl Microbiol Biotechnol 90:1229-1239.

The teachings of all patents, published applications, and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. An extract from the hairy root of a *Morinda officinalis* How plant transformed by an *Agrobacterium rhizogenes* bacterium comprising an expression vector comprising a nucleic acid molecule comprising a nucleotide sequence having at least 90% sequence identity to the cDNA nucleotide sequence of SEQ ID NO:1; and/or encoding an amino acid sequence having at least 90% sequence identity to the amino acid sequence of SEQ ID NO:2.

2. The extract of claim 1, wherein the nucleotide sequence has at least 95% sequence identity to the cDNA nucleotide sequence of SEQ ID NO:1.

3. The extract of claim 1, wherein the nucleotide sequence has 100% sequence identity to the cDNA nucleotide sequence of SEQ ID NO:1.

4. The extract of claim 1, wherein the amino acid sequence has at least 95% sequence identity to the amino acid sequence of SEQ ID NO:2.

5. The extract of claim 1, wherein the amino acid sequence has 100% sequence identity the amino acid sequence of SEQ ID NO:2.

6. A method of treating an inflammatory bowel disease in a subject comprising administering to the subject an effective amount of the extract of claim 1.

7. An extract from the hairy root of a *Morinda officinalis* How plant transformed by an *Aqrobacterium rhizogenes* bacterium comprising an expression vector comprising a promoter and a nucleic acid molecule comprising a nucleotide sequence having at least 90% sequence identity to the cDNA nucleotide sequence of SEQ ID NO:1; and/or encoding an amino acid sequence having at least 90% sequence identity to the amino acid sequence of SEQ ID NO:2, wherein the promoter is not natural to *Eucalyptus camaldulensis*.

8. The extract of claim 7, wherein the nucleotide sequence has at least 95% sequence identity to the cDNA nucleotide sequence of SEQ ID NO:1.

9. The extract of claim 7, wherein the nucleotide sequence has 100% sequence identity to the cDNA nucleotide sequence of SEQ ID NO:1.

10. The extract of claim 7, wherein the amino acid sequence has at least 95% sequence identity to the amino acid sequence of SEQ ID NO:2.

11. The extract of claim 7, wherein the amino acid sequence has 100% sequence identity to the amino acid sequence of SEQ ID NO:2.

12. A method of treating an inflammatory bowel disease in a subject comprising administering to the subject an effective amount of the extract of claim 7.

\* \* \* \* \*

SEQUENCE LISTING

<160> NUMBER OF SEQ ID NOS: 2

<210> SEQ ID NO 1
<211> LENGTH: 1529
<212> TYPE: DNA
<213> ORGANISM: Eucalyptus camaldulensis

<400> SEQUENCE: 1

```
atggtgagcg tcgaggaatt ctgccgtgcc cagaaatcga aaggccctgc ctcggtcctc      60
gccatcggaa cggcggtccc caagaacgtc atcgagcaga gcacatacccc ggattatttg    120 tttcggatca ccaacagcga gcacatgacc gagctgaaag agaagttcaa gcgcatgtgt    180
atgtatagtt caaagcatac ctacattgat gctctttcat ttatatgtaa ttttttttgct   240 gcgccctcat catttatcat cacgtaagaa tttgccggat tcacttcatc tagcgtatcc    300
atgctttaga taagaaatta aggaaagacg gtgaaagcaa atcaacagta gtttcgatgg    360
gagttcccga tgccaggatc ggttttcttc cggtaataac ttgtggggtc attgaaaaga    420
ttgcgcccct catcgtcgcg taccattagc tcgatcggtc cgtagagaag gactataaaa    480
aaggcgtcgc aggggctcat tgacatgggg tctgtgtttg gtttgtgtat gtttcaggtg    540
aggggtcgtc gatcaagagg agatacgtgc acatgacgga ggatatattg aaagagcacc    600
cgagcatgag ttcattcacg gaaccctcct tggatgcccg gcacgacatc ctggtgtcgg    660
```

```
aagtgccgaa gctggcgaag gaggcggcgg cgaacgccct gaaggaatgg gggcagccca    720
agtcgaagat cacccacctg gtgttctgca ccaccagcgg tgtcgacatg ccgggctgcg    780
actaccagct caccaagctc ctgggcctcc gccccaccgt caagcggtac atgatgtacc    840
aggtgggctg ctacggcgct ggcctggtcc tccgcatcgc cagggatctt gctgagaaca    900 acaaggggc tcgcgtcctc gtcgtgtgcg ccgagatcac cgtctgcacc ttccgcggcc     960
ccaccgagac ctacctggac aacctcgtgg gccaggctct gttcggcgat ggcgcctcct   1020
cggtcatcgt gggctcggac cccgtcccgg gggtcgagag gcccctgtac gagatcgtct   1080
ccacctccca gactctcctc ccaaacagcg agggggccat tgctgggcac gtccgggaga   1140
tcgggctcac catccacctc ctcaaggacg tgccgggcct catctccaag aacgtcgaga   1200
agaacatgac tgaggcgttc cacccactgg gcatcaccga ctggaactcg ctcttcttca   1260
tcgtgcaccc cggcgggccc gcgattctcg acgaggtcga ggccaagttg aagctcaagc   1320
ccgagaagat ggaggcttcc aggtatgtgc tcggcgagta tggcaacatg tctagcgcat   1380
gcgtcttctt cataatggac gagatgagga agaaatcgat caagaaaggg ctcaagacca   1440
ctggagaggg gctcgaatgg ggcgtgctct tcggatttgg tcccggcctc accgtcgaga   1500
ccgtcgtcct ccacgccctg tctgcttaa                                     1529
```

<210> SEQ ID NO 2
<211> LENGTH: 389
<212> TYPE: PRT
<213> ORGANISM: Eucalyptus camaldulensis

<400> SEQUENCE: 2

```
Met Val Ser Val Glu Glu Phe Cys Arg Ala Gln Lys Ser Lys Gly Pro
1               5                   10                  15

Ala Ser Val Leu Ala Ile Gly Thr Ala Val Pro Lys Asn Val Ile Glu
            20                  25                  30

Gln Ser Thr Tyr Pro Asp Tyr Leu Phe Arg Ile Thr Asn Ser Glu His
        35                  40                  45

Met Thr Glu Leu Lys Glu Lys Phe Lys Arg Met Cys Glu Gly Ser Ser
    50                  55                  60

Ile Lys Arg Arg Tyr Val His Met Thr Glu Asp Ile Leu Lys Glu His
65                  70                  75                  80

Pro Ser Met Ser Ser Phe Thr Glu Pro Ser Leu Asp Ala Arg His Asp
                85                  90                  95

Ile Leu Val Ser Glu Val Pro Lys Leu Ala Lys Glu Ala Ala Asn
            100                 105                 110

Ala Leu Lys Glu Trp Gly Gln Pro Lys Ser Lys Ile Thr His Leu Val
        115                 120                 125

Phe Cys Thr Thr Ser Gly Val Asp Met Pro Gly Cys Asp Tyr Gln Leu
    130                 135                 140

Thr Lys Leu Leu Gly Leu Arg Pro Thr Val Lys Arg Tyr Met Met Tyr
145                 150                 155                 160

Gln Val Gly Cys Tyr Gly Ala Gly Leu Val Leu Arg Ile Ala Lys Asp
                165                 170                 175

Leu Ala Glu Asn Asn Lys Gly Ala Arg Val Leu Val Cys Ala Glu
            180                 185                 190

Ile Thr Val Cys Thr Phe Arg Gly Pro Thr Glu Thr Tyr Leu Asp Asn
        195                 200                 205

Leu Val Gly Gln Ala Leu Phe Gly Asp Gly Ala Ser Ser Val Ile Val
```

-continued

```
              210                 215                 220
Gly Ser Asp Pro Val Pro Gly Val Glu Arg Pro Leu Tyr Glu Ile Val
225                 230                 235                 240

Ser Thr Ser Gln Thr Leu Leu Pro Asn Ser Glu Gly Ala Ile Ala Gly
                245                 250                 255

His Val Arg Glu Ile Gly Leu Thr Ile His Leu Leu Lys Asp Val Pro
                260                 265                 270

Gly Leu Ile Ser Lys Asn Val Glu Lys Asn Met Thr Glu Ala Phe His
                275                 280                 285

Pro Leu Gly Ile Thr Asp Trp Asn Ser Leu Phe Phe Ile Val His Pro
                290                 295                 300

Gly Gly Pro Ala Ile Leu Asp Glu Val Glu Ala Lys Leu Lys Leu Lys
305                 310                 315                 320

Pro Glu Lys Met Glu Ala Ser Arg Tyr Val Leu Gly Glu Tyr Gly Asn
                325                 330                 335

Met Ser Ser Ala Cys Val Phe Phe Ile Met Asp Glu Met Arg Lys Lys
                340                 345                 350

Ser Ile Lys Lys Gly Leu Lys Thr Thr Gly Glu Gly Leu Glu Trp Gly
                355                 360                 365

Val Leu Phe Gly Phe Gly Pro Gly Leu Thr Val Glu Thr Val Val Leu
                370                 375                 380

His Ala Leu Ser Ala
385
```